(12) United States Patent
Bichon et al.

(10) Patent No.: US 11,253,462 B2
(45) Date of Patent: Feb. 22, 2022

(54) COSMETIC COMPOSITION COMPRISING A PULLULAN DERIVATIVE

(71) Applicant: LVMH RECHERCHE, Saint Jean de Braye (FR)

(72) Inventors: Yohann Bichon, Maisons-Alfort (FR); Caroline Koussouros, Orleans (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 32 days.

(21) Appl. No.: 16/619,035

(22) PCT Filed: Dec. 13, 2018

(86) PCT No.: PCT/FR2018/053256
§ 371 (c)(1),
(2) Date: Dec. 3, 2019

(87) PCT Pub. No.: WO2019/115949
PCT Pub. Date: Jun. 20, 2019

(65) Prior Publication Data
US 2020/0138692 A1 May 7, 2020

(30) Foreign Application Priority Data
Dec. 15, 2017 (FR) ..................................... 1762272

(51) Int. Cl.
| | | |
|---|---|---|
| *A61K 8/895* | (2006.01) | |
| *A61K 8/25* | (2006.01) | |
| *A61K 8/29* | (2006.01) | |
| *A61K 8/31* | (2006.01) | |
| *A61K 8/81* | (2006.01) | |
| *A61K 8/92* | (2006.01) | |
| *A61Q 1/06* | (2006.01) | |
| *A61Q 1/10* | (2006.01) | |
| *A61Q 1/12* | (2006.01) | |

(52) U.S. Cl.
CPC ................ *A61K 8/895* (2013.01); *A61K 8/25* (2013.01); *A61K 8/29* (2013.01); *A61K 8/31* (2013.01); *A61K 8/8105* (2013.01); *A61K 8/8129* (2013.01); *A61K 8/8135* (2013.01); *A61K 8/8147* (2013.01); *A61K 8/8182* (2013.01); *A61K 8/922* (2013.01); *A61K 8/925* (2013.01); *A61Q 1/06* (2013.01); *A61Q 1/10* (2013.01); *A61Q 1/12* (2013.01); *A61K 2800/412* (2013.01); *A61K 2800/436* (2013.01); *A61K 2800/59* (2013.01); *A61K 2800/87* (2013.01)

(58) Field of Classification Search
CPC . A61K 8/895; A61K 8/25; A61K 8/29; A61K 8/31; A61K 8/8105; A61K 8/8129; A61K 8/8135; A61K 8/8147; A61K 8/8182; A61K 8/922; A61K 8/925; A61K 2800/412; A61K 2800/436; A61K 2800/59; A61K 2800/87; A61K 8/891; A61K 8/731; A61Q 1/06; A61Q 1/10; A61Q 1/12
See application file for complete search history.

(56) References Cited

U.S. PATENT DOCUMENTS

| | | |
|---|---|---|
| 4,970,252 A | 11/1990 | Sakuta et al. |
| 2003/0082221 A1 | 5/2003 | O'Halloran et al. |
| 2009/0068255 A1* | 3/2009 | Yu et al. ............... A61Q 19/005 424/450 |
| 2011/0268675 A1* | 11/2011 | Ureneck ................ A61K 8/585 424/59 |
| 2016/0113860 A1 | 4/2016 | Kikuchi |

FOREIGN PATENT DOCUMENTS

| | | |
|---|---|---|
| FR | 2910285 | 6/2008 |
| FR | 3058888 | 5/2018 |
| JP | 2004244333 | 9/2004 |
| JP | 2005325088 | 11/2005 |
| KR | 20150100201 | 9/2015 |
| KR | 101666267 | 10/2016 |
| WO | 2014181747 | 11/2014 |

OTHER PUBLICATIONS

Pascal et al. (FR2910285A1 Machine translation) (Year: 2008).*
"Liquid Concealer Aura Veil," GNPD, MINTEL, Sep. 4, 2017, XP002773370 (4 pages).
International Search Report and Written Opinion issued for International Patent Application No. PCT/FR2018/053256, dated Feb. 14, 2019, 14 pages including English translation of Search Report.

* cited by examiner

*Primary Examiner* — Quanglong N Truong
(74) *Attorney, Agent, or Firm* — Hamre, Schumann, Mueller & Larson, P.C.

(57) ABSTRACT

The invention relates to a composition comprising:
(i) a trialkylsiloxysilylcarbamoyl pullulan compound,
(ii) a polymethyl methacrylate polymer,
(iii) a mattifying substance, and
(iv) at least one volatile hydrocarbon oil.
The invention is also targeted at the use of such a composition for making up and/or caring for keratinous substances, the skin and the lips, and more particularly in mascaras, foundations and lipsticks.

36 Claims, No Drawings

COSMETIC COMPOSITION COMPRISING A PULLULAN DERIVATIVE

The present invention relates to a novel cosmetic composition and to its use in the care or makeup field. The invention more particularly relates to a novel composition comprising a mixture of ingredients based on trialkylsiloxysilylcarbamoyl pullulan, on at least one silicone polymer, a mattifying filler and at least one volatile oil.

The invention is also targeted at compositions and methods for making up and/or caring for keratinous substances or the skin, comprising a stage of application of a composition according to the invention in order to form a film. Mascaras comprising a composition according to the invention are also subject matters of the invention. Finally, a makeup kit comprising such a composition also comes within the invention.

STATE OF THE PRIOR ART AND PURPOSES OF THE INVENTION

Cosmetic compositions for making up and/or caring for the skin or keratinous substances, such as the eyelashes or the eyebrows, have to meet a complex specification comprising a multitude of criteria. Mention may be made, for example, of the stability and the hold of the product over time, the comfort during its application and over time, once applied. These criteria are difficult to satisfy simultaneously: for example, increasing the hold of a makeup product very frequently results in a decrease in the comfort felt by the user, related to a dryness, tacky feelings or a heaviness of the deposit on the keratinous substances, the skin or the lips. It is possible, for example, to use waxes in order to thicken the film and to give a more viscous texture to the composition during its application. The disadvantage of the waxes is that they exactly render the film more rigid and tacky, which produces a feeling of discomfort on application and throughout the day.

A purpose of the invention is to maintain the hold (adhesion) of makeup and/or care products over a long period of time, that is to say for at least 24 hours, advantageously 36 hours, while retaining their flexibility and their comfort on application.

Pullulan is known from the application US 2003/0082221 for its use as nontacky film-forming agent in the cosmetics field. Pullulan is a natural polysaccharide, a polymer consisting of maltotriose units, a glucose triholoside, also known as α-1,4-; α-1,6-glucan. Pullulan is produced from starch by the fungus *Aureobasidium pullulans*.

Pullulan silicone derivatives of the trialkylsiloxysilylcarbamoyl pullulan type are commonly used in makeup products. The application KR2015100201 describes, for example, very mild water-in-oil emulsions based on urethane polymer, on one or more entities chosen from a silicone resin, trimethylsiloxysilylcarbamoyl pullulan and a silicone-acrylic copolymer, and a silicone gum or a silicone polymer.

The application WO2014181747=US2016/113860 also describes cosmetic compositions based on trimethylsiloxysilylcarbamoyl pullulan which are easy to apply and which exhibit a good hold without a tacky effect, and also a good retention effect. This document is not relevant in particular as it uses a volatile silicone oil consisting of decamethylcyclopentasiloxane, whereas the invention described below uses mainly or exclusively a volatile hydrocarbon oil.

Likewise, the abridged document XP00277, relating to a commercial product called "Liquid ConcealerAura Veil", is also not relevant in particular as it uses a volatile silicone oil consisting of cyclomethicone and cyclopentasiloxane, whereas the invention described below uses mainly or exclusively a volatile hydrocarbon oil.

Again, the document JP 2005/325088 Shiseido uses a volatile silicone oil consisting of decamethylcyclopentasiloxane, whereas the invention described below uses mainly or exclusively a volatile hydrocarbon oil.

The document JP 2004/244333 does not contain silicone polymer, unlike the present invention, in addition combined with a volatile hydrocarbon oil.

Also, the document FR 2 910 285 (L'Oréal) relates to a cosmetic kit comprising a catalyst or a peroxide with a compound X and a compound Y capable of reacting together in the presence of the catalyst and formulated according to 2 different compositions, utterly remote from the present invention.

Furthermore, the applicant has described, in the application FR 16 62634, filed with priority date of Nov. 23, 2016, the combination of a pullulan silicone derivative with a specific acrylate copolymer and a specific polysilsesquioxane resin in order to obtain compositions exhibiting a markedly improved hold, or adhesion, over time.

One of the objectives of the present invention consists in providing a novel cosmetic composition for making up and/or caring for the skin, lips or keratinous substances forming, during its application, a film combining lengthy hold, in particular of greater than 24 hours, and comfort on application. It is unexpectedly that the inventors have discovered that the combination of a trialkylsiloxysilylcarbamoyl pullulan compound with a silicone polymer and a mattifying filler, in the presence of at least one volatile oil, results in a synergistic effect for obtaining cosmetic compositions which leave, on the skin, lips or keratinous substances, a film, the flexible and light texture of which produces a nongreasy and nontacky feeling of softness without a cardboard effect, while exhibiting a significantly improved adhesion (hold), and thus a superior resistance to water, to sebum, to sweat and to rubbing actions than that of the compositions of the prior art. By virtue of this combination of ingredients, the inventors have unexpectedly shown that it is entirely possible to reduce the amount of waxes to a maximum of 5% by weight of the composition and more advantageously still to exclude waxes from said compositions, and thus to limit the disadvantages thereof known to a person skilled in the art, which are in particular feelings of heaviness and of discomfort during and after application of the composition. It is thus possible to obtain compositions having a low content of and better still devoid of waxes, the hold and comfort on application properties of which are particularly noteworthy.

Besides these improved properties, the compositions of the invention produce a "matte" makeup effect, this mattness being particularly advantageous for application to keratinous fibers, in particular the eyelashes or the eyebrows.

DESCRIPTION OF THE INVENTION

Definitions

Within the meaning of the invention, the term "keratinous substances" is targeted at human keratinous fibers, such as the eyelashes, eyebrows or hair, and artificial keratinous fibers, such as false eyelashes. A makeup composition intended to be applied to these keratinous fibers is also known as "mascara".

In the present patent application, the expressions "from . . . to . . ." and "between . . . and . . ." are targeted at comprising the upper and lower limits of the range of values. The disclosure of a range of values excluding its limits is equivalent to disclosure of the equivalent range of values including the limits, and vice versa.

The term "film-forming polymer" is understood to mean a polymer capable of forming a continuous film on a support. In the text, the word polymer can denote a homopolymer or a copolymer. The term "copolymer" is understood to mean a polymer comprising at least two different monomers or two different blocks, which can be of the same chemical family but of different structure.

The terms "silicone polymer" or "crosslinked silicone polymer" denote the same family of ingredients in the present description.

An "oil", within the meaning of the present invention, can be defined as a compound which is insoluble in water (solubility of less than 0.05 mg/I at 20° C.) and liquid at ambient temperature (25° C.), the melting point, the softening point and the glass transition point at atmospheric pressure of which is less than or equal to 30° C., preferably less than or equal to 25° C.

The volatility can be defined, in the context of the invention, for example, by a vapor pressure measurable by an empirical method at 25° C., the value of which will be between 0.13 Pa and 40 000 Pa, for example between 1 Pa and 20 000 Pa, between 10 Pa and 8000 Pa, indeed even between 15 and 150 Pa. The vapor pressure will be measured according to one of the methods most suitable for the compound of interest, which methods appear in the Guidelines of the Test No. 104 of the OECD (2006 version). It is alternatively possible to choose a volatile oil exhibiting a boiling point at atmospheric pressure of less than 250° C., according to an alternative form of less than 230° C. and according to another alternative form of between 150° C. and 220° C. The volatile oil can also be defined as a compound having a flash point ranging from 35° C. to 100° C., in particular between 40° C. and 80° C.

Isododecane, which is regarded in the present patent application as a volatile oil, has a boiling point at 105 Pa of between 175° C. and 195° C., a flashpoint of 45° C. and a vapor pressure at 20° C. equal to 100 Pa. Its solubility in water at 20° C. is less than or equal to $1.0 \times 10^{-2}$ mg/I.

Cyclopentadimethylsiloxane, regarded as another volatile oil, has a solubility in water at 25° C. equal to $1.7 \times 10^{-2}$ mg/I, a flash point of 77° C., a boiling point at 105 Pa equal to 205° C. and a vapor pressure equal to 26 Pa at 25° C.

Aspects of the Invention

According to a first aspect, a subject matter of the invention is a cosmetic composition comprising:
(i) a trialkylsiloxysilylcarbamoyl pullulan compound,
(ii) a silicone polymer,
(iii) a mattifying filler, and
(iv) at least one volatile hydrocarbon oil.

The trialkylsiloxysilylcarbamoyl pullulan compound (i) can represent from 0.5% to 30% by weight of the composition, according to an alternative form from 1% to 15% and according to another alternative form from 1% to 5%, by weight, of the total weight of the composition.

The silicone polymer can represent from 0.1% to 30% by weight of the composition, according to an alternative form from 0.5% to 15% and according to another alternative form from 1% to 10%, by weight, of the total weight of the composition.

The mattifying filler (iii) can represent from 0.5% to 30% by weight of the composition, according to an alternative form from 0.5% to 15%, according to another alternative form from 2% to 10%, by weight of the total weight of the composition, and The volatile hydrocarbon oil (iv) can represent from 10% to 70% by weight of the composition, according to an alternative form from 15% to 65% and according to another alternative form from 20% to 60%, by weight, of the total weight of the composition.

According to an alternative form of the invention, the volatile hydrocarbon oil represents the balance to 100% by weight of the composition comprising the ingredients (i) to (iv).

According to a specific embodiment of the invention, the cosmetic composition comprises, as percentage by weight of the composition:
(i) from 0.5% to 30% by weight of a trialkylsiloxysilylcarbamoyl pullulan compound,
(ii) from 0.1% to 30% by weight of a silicone polymer,
(iii) from 0.5% to 30% by weight of a mattifying filler, and
(iv) at least one volatile hydrocarbon oil, In another specific embodiment of the invention, the ratio by weight of the components (i), (ii) and (iii) is within the range 1/1/1 to 1/5/10 and more particularly still within the range 1/1/3 to 1/2/4. According to an even more specific embodiment, it is of the order of 1/2/2.

According to these specific embodiments of the invention, the composition exhibits the advantage, once applied to the skin, lips or keratinous fibers, in particular the eyelashes and eyebrows, of forming a high-hold film producing an entirely surprising matte effect and a noteworthy feeling of comfort.

The Trialkylsiloxysilylcarbamoyl Pullulan (i)

The trialkylsiloxysilylcarbamoyl pullulan compound (i) is described in the application US 2003/0082221 and also in the application KR2015100201 and again in the application WO2014181747 relating to cosmetic compositions, and in particular mascara compositions, based on trimethylsiloxysilylcarbamoyl pullulan, which are easy to apply and exhibit a good hold, without a tacky effect, and also a good retention effect.

According to a specific embodiment of the invention, the trialkylsiloxysilylcarbamoyl pullulan compound comprises alkyl groups comprising from 1 to 6 carbon atoms. These alkyl groups can be linear or branched. According to another specific embodiment, the trialkylsiloxysilylcarbamoyl pullulan of the invention is trimethylsiloxysilylcarbamoyl pullulan.

Thus, according to another specific embodiment of the invention, the composition according to the invention comprises, as percentage by weight of the composition:
(i) from 1 to 15 of trimethylsiloxysilylcarbamoyl pullulan,
(ii) from 0.5 to 15 of a silicone polymer,
(iii) from 1 to 15 of a mattifying filler, and
(iv) from 10 to 70 of at least one volatile hydrocarbon oil, which can in particular constitute the balance of the mixture of the compounds (i) to (iv).

The Silicone Polymer (ii)

In the composition of the invention, the silicone polymer (ii) is, according to a specific alternative embodiment, a nongelled or gelled crosslinked silicone polymer.

The crosslinked silicone polymer can be dispersed or gelled by an oil. It is preferable for it to be in the form of gelled or dispersed particles, the mean size of which is between 10 and 200 microns. The crosslinked silicone polymer may be denoted as being an elastomer by a person skilled in the art.

The expressions "gelled or dispersed crosslinked silicone polymer" and "gelled or dispersed crosslinked silicone polymer particles" are used without distinction in the present description. It is understood that "gelled" denotes "gelled" by an oil. The expression "crosslinked silicone polymer" can denote the crosslinked silicone polymer gelled or dispersed in an oil.

The crosslinked silicone polymer can be obtained by reaction of an organopolysiloxane containing in particular at least one —Si—H group in the end position with an organopolysiloxane comprising at least one ethylenically unsaturated group bonded to a silicon atom and better still at least two ethylenically unsaturated groups bonded to said silicon atom. The ethylenically unsaturated group can be chosen from vinyl, allyl and propenyl groups; it is in particular located at the ends of the organopolysiloxane molecule.

The crosslinked silicone polymer can be obtained by a hydrosilylation reaction of the two abovementioned organopolysiloxanes, in the presence of a catalyst and of an oil, under reaction conditions known to a person skilled in the art. The catalyst can be hexachloroplatinic acid or a platinum complex.

It will alternatively be possible to use a crosslinked silicone polymer obtained by a dehydrogenation crosslinking condensation reaction between the two organopolysiloxanes described above, in the presence of a catalyst and of an oil.

The oil used in the preparation of the crosslinked silicone polymer can be a nonvolatile oil or a volatile oil identical to one of the volatile oils described below participating in the composition of the product of the invention. Mention will be made, as an example, of isododecane or decamethylcyclopentasiloxane.

According to an alternative embodiment, one at least of the abovementioned organopolysiloxanes predominantly comprises dimethylsiloxane units, it being possible for the other units to be methylphenylsiloxane or dimethylvinylsiloxy units for a vinyl organosiloxane and methylhydrosiloxane units for the organopolysiloxane containing —Si—H groups.

The organopolysiloxane comprising at least one ethylenically unsaturated group bonded to a silicon atom can be chosen from copolymers, a part of the units of which comprise vinyl groups or for which at least one vinyl group is in the end position of the chain.

The organopolysiloxane comprising at least one vinyl group can be chosen from methylvinylsiloxane/dimethylsiloxane copolymers, polydimethylsiloxanes comprising dimethylvinylsiloxy end groups, dimethylsiloxane/methylphenylsiloxane copolymers comprising dimethylvinylsiloxy end groups, and dimethylsiloxane/methylvinylsiloxane copolymers comprising trimethylsiloxy end groups.

The organopolysiloxane containing —Si—H groups and the organopolysiloxane comprising at least two end vinyl groups are in particular used in proportions such that the molar ratio of the total amount of hydrogen atoms bonded to silicon atoms to the total amount of the vinyl groups is between 1.5/1 and 20/1.

The organopolysiloxane containing —Si—H groups can be a polydimethylsiloxane or a poly(dimethyl)(methylhydro)siloxane, one or the other comprising at least one Si—H bond at the chain end.

The crosslinked silicone polymer is, for example, the reaction product of a polydimethylsiloxane or of a poly (dimethyl)(methylhydro)siloxane, one or the other comprising at least one end Si—H bond, with a polydimethylsiloxane comprising two vinyl groups, in particular located at the end position of the chain.

According to an alternative form of the invention, the silicone polymer is a silicone elastomer exhibiting viscoelastic properties. The silicone elastomer used in the present invention improves the feel of the composition (soft focus effect). Said silicone elastomer is, according to one embodiment, chosen from polydimethylsiloxane (PDMS) (or dimethicone), methylpolysiloxane (MQ), vinyl methylpolysiloxane (VMQ), phenylvinylmethylpolysiloxane (PVMQ), fluorovinylmethylpolysiloxane (FVMQ) and their mixtures. The silicone elastomer of the invention is generally provided in the form of a gel, of a paste or of a powder.

The crosslinked silicone powder is, according to a specific embodiment, in the form of a gel in the composition.

For example, the silicone polymer gel comprises gelled crosslinked silicone polymer particles trapping molecules of an oil, which oil can represent between 10% and 95% by weight of the weight of the gel. The proportion of oil present in the gel can vary from 60% to 95% by weight, for example from 80% to 90% by weight. Such a crosslinked silicone polymer gel can be manufactured by applying high shearing to crosslinked silicone polymer particles, which have been presynthesized from the two organopolysiloxanes described above, said shearing being exerted in the presence of an oil. The shearing can be carried out in a high-pressure homogenizer, so as to obtain polymer particles gelled by said oil; their size can vary between 10 and 200 microns. Reference will be made without distinction to a crosslinked silicone polymer gel in an oil or to crosslinked silicone polymer particles gelled by an oil.

The gelling agent for the crosslinked silicone polymer particles can be a nonvolatile oil or preferably a volatile oil chosen from volatile hydrocarbon oils, volatile silicone oils or one of their mixtures, these oils being, in accordance with the description, volatile oils mentioned above or below in the description.

A person skilled in the art will be able to confirm, by conventional methods, that the crosslinked silicone polymer is gelled or dispersed in the composition.

The present patent application describes a crosslinked silicone polymer obtained by reaction of a polymethylhydrosiloxane comprising trimethylsiloxy end groups or of a poly(dimethyl)(methylhydro)siloxane comprising trimethylsiloxy end groups with a polydimethylsiloxane comprising two vinyl groups, for example two vinyl end groups (i.e. polydimethylsiloxane comprising dimethylvinylsiloxy end groups), in the presence of a platinum catalyst. Some of these compounds are described in the patent U.S. Pat. No. 4,970,252.

Use may in particular be made of a crosslinked silicone polymer, the INCI name of which corresponds to polysilicone-11. According to a preferred alternative form of the invention, use is made of polysilicone-11 dispersed with isododecane.

The Mattifying Filler (iii)

The composition according to the invention comprises at least one mattifying filler.

The mattifying filler, according to a specific embodiment, consists of a solid filler in the pulverulent or powder form. Within the meaning of the invention, the term "filler" should be understood as meaning a mass of particles of inorganic or organic and natural or synthetic nature which is provided in a form which is insoluble and dispersed in the medium of the composition.

As the name indicates, the "mattifying" filler makes it possible to obtain a matte effect once the film has been formed after application. This mattness effect is particularly important when it is desired to avoid a shiny makeup rendering. This is in particular the case when the composition is applied to the eyelashes or the eyebrows. This mattifying filler, by the effect which it produces, also makes it possible, when the composition is applied to the skin, to soften the imperfections of the skin, such as the wrinkles or fine lines which gradually appear with age.

The mattifying filler can at least partially consist of particles treated at the surface with a hydrophilic or lipophilic organic agent in order to facilitate their incorporation in one or the other phase of the composition, in particular in order to disperse the particles homogeneously in oily phases and more generally in liquid phases, the viscosity of which may be high.

According to a specific embodiment of the invention, the mattifying filler consists of non-spherical or spherical particles, with regular or irregular outlines, or else hemispherical or platelet particles, having a volume-median size, denoted $D_{50}$, of less than or equal to 25 µm, in particular of less than or equal to 15 µm, especially of less than or equal to 10 µm.

The term "volume-medium size" denotes the dimension given by the statistical particle size distribution at half the population, referred to as $D_{50}$, measured with a Malvern Mastersizer laser particle sizer.

According to various alternative embodiments, the mattifying filler (iii) consists of a solid filler in the pulverulent (or powder) form chosen from the group consisting of:
cellulose powders, cellulose beads,
microcrystalline cellulose powders,
silica and silicate powders, amorphous silica microspheres, silica microbeads,
silica/$TiO_2$ composite powders,
talc/$TiO_2$/alumina/silica composite powders,
polymethyl methacrylate (PMMA) powders,
boron nitride powders,
crosslinked elastomeric organopolysiloxane powders coated or not coated with silicone resin,
hydrophobic silica aerogel powders,
nylon powders,
starch powders,
powders of vegetable origin, such as rice powders, cotton powders or silk powders,
talcs, natural and synthetic micas, sericites, borosilicates and their mixtures,
and their mixtures.

According to various specific embodiments, use may be made, as all or part of the mattifying filler, of:
cellulose powders with irregular outlines, such as those sold by Daito Kasei under the name Cellulobeads USF;
crosslinked elastomeric organopolysiloxane powders coated with silicone resin, in particular with silsesquioxane resin, such as the powders with the INCI name "Vinyl dimethicone/methicone silsesquioxane crosspolymer PEG-7 glyceryl cocoate, Polyquaternium-7 and methylsilanol tri-PEG-8 glyceryl cocoate" sold by Miyoshi Kasei under the name MW-SRP-100;
PMMA powders, such as the powder with the INCI name "methyl methacrylate crosspolymer" from Sunjin under the name Sunpmma-X or Makibeads 150 from Daito Kasei;
hydrophobic silica aerogel particles with the INCI name Silica silylates sold by Dow Corning under the name Dow Corning VM-2270 aerogel fine particles;
micas, such as that sold under the name Submica M by Sensient;
and their mixture(s).

According to another specific embodiment, use will be made, as mattifying filler, of one or more polymethyl methacrylate (PMMA) powder(s), one or more mica(s) or their mixture(s).

The Volatile Oil (iv)

The composition of the invention comprises at least one volatile hydrocarbon oil (iv).

The volatile oil is capable of evaporating on contact with the skin in less than one hour, at ambient temperature (25° C.) and atmospheric pressure (750 mmHg, i.e. 105 Pa). The presence of at least one volatile oil in the composition of the invention is essential in that it makes possible, by its rapid evaporation at the time of the application of the composition to a support, such as the skin or keratinous substances, the progressive formation of a film in situ.

This film then produces the desired visual or care effect. That formed by the composition also exhibits a flexible texture which provides a noteworthy comfort and a hold for greater than 24 h.

The volatile hydrocarbon oil (iv) of the invention can, according to an alternative embodiment, be mixed with a silicone oil. It can be of animal, vegetable, mineral or synthetic origin.

Within the meaning of the present invention, the term "silicone oil" is understood to mean a compound comprising at least one silicon atom and in particular at least one Si—O group.

The term "hydrocarbon oil" is understood to mean an oil containing mainly hydrogen and carbon atoms.

The oils can optionally comprise oxygen, nitrogen, sulfur and/or phosphorus atoms, for example in the form of hydroxyl or acid radicals.

Mention may in particular be made, among volatile hydrocarbon oils, of branched alkanes having from 8 to 16 carbon atoms, such as isoalkanes (also known as isoparaffins) having from 8 to 16 carbon atoms, such as isododecane, isodecane or isohexadecane, branched esters having from 8 to 16 carbon atoms, such as isohexyl neopentanoate, and their mixtures. According to a specific embodiment, a volatile hydrocarbon oil comprises or consists of isododecane. Mention may also be made of linear alkanes having from 8 to 16 carbon atoms, in particular from 10 to 15 carbon atoms and more particularly from 11 to 13 carbon atoms.

Mention may be made, as volatile silicone oils, of linear silicone oils, such as hexamethyldisiloxane, octamethyltrisiloxane, decamethyltetrasiloxane, tetradecamethylhexasiloxane, hexadecamethylheptasiloxane and dodecamethylpentasiloxane. Mention may be made, as volatile cyclic silicone oils, of cyclopentasiloxane, hexamethylcyclotrisiloxane, octamethylcylotetrasiloxane, decamethylcyclopentasiloxane and dodecamethylcyclohexasiloxane.

According to a specific embodiment of the invention, a volatile hydrocarbon oil (iv) is chosen from isododecane, isohexadecane and their mixtures with a volatile silicone oil, for example cyclopentasiloxane.

According to a specific alternative embodiment, the volatile oil (iv) comprises or consists of isododecane.

According to another specific embodiment of the invention, the cosmetic composition comprises, as percentage by weight of the composition:
(i) from 0.5% to 30% by weight of a trimethylsiloxysilylcarbamoyl pullulan compound,
(ii) from 0.1% to 30% by weight of polysilicone-11, (iii) from 0.5% to 30% by weight of a mattifying filler consisting of mica and/or of polymethyl methacrylate (PMMA) and (iv) isododecane, in particular from 10% to 70% by weight of at least isododecane, which can in particular constitute the balance of the mixture of the compounds (i) to (iv).

Adjuvants of the Composition

Besides the compounds (i), (ii), (iii) and (iv) described above, the composition can comprise one or more adjuvants or additional components which make it possible to improve the composition with regard to criteria such as the chemical or microbiological stability, the visual or olfactory aspect or the rheological behavior or else to confer, on this composition, a cosmetic activity, for example a moisturizing and/or anti-aging activity, without detrimentally affecting the essential properties forming the basis of the invention, such as the hold, the mattness or the comfort of the film formed by said composition after application to a support.

According to a specific embodiment of the invention, the composition can thus also comprise a nonvolatile hydrocarbon or silicone oil of natural or synthetic origin.

This nonvolatile oil is in particular of use in dispersing the pigments used in the composition of the invention in order to produce a visual makeup effect.

The nonvolatile oil can be present in an amount of between 0.5% and 15%, in particular between 0.5% and 10% and better still between 0.5% and 5%.

According to another specific embodiment of the invention, the composition comprises from 0% to 5% by weight of a wax, according to one alternative form up to 2% by weight.

According to yet another embodiment of the invention, the composition is devoid of wax.

The wax can, for example, be chosen from:
"non-polar" waxes, such as microcrystalline waxes, paraffin waxes, ozokerite, polyethylene waxes, silicone waxes and fluorinated waxes, and
"polar" waxes, such as, for example, beeswax, rice bran wax, carnauba wax, candelilla wax, ouricury wax, Japan wax, berry wax, sumac wax, montan wax, esparto wax, cork fiber wax, sugarcane wax, orange wax, lemon wax, laurel wax, the waxes obtained by hydrogenation of animal or vegetable oils having linear or branched $C_8$-$C_{32}$ fatty chains, such as jojoba oil, sunflower oil, castor oil, coconut oil, lanolin oil, olive oil esterified with stearyl alcohol or castor oil esterified with cetyl alcohol, and
their mixture(s).

According to an alternative form of the invention, the composition can comprise from 0% to 20% of water.

According to a first specific embodiment of the invention, the composition is anhydrous. The anhydrous composition according to the invention makes it possible to obtain, at the time of the application, a film which is formed particularly rapidly and the mechanical properties of which are noteworthy.

According to a second embodiment, the composition can comprise an aqueous phase dispersed in a continuous phase (water-in-oil emulsion).

According to another specific embodiment, the composition of the invention can also comprise a nonsilicone film-forming polymer. The nonsilicone film-forming polymer can be of natural or synthetic origin and is chosen in particular from:
copolymers of vinylpyrrolidone (VP) and preferably copolymers of VP and of $C_2$-$C_{20}$ alkene, such as VP/eicosene, VP/vinyl acetate, VP/ethyl methacrylate, VP/ethyl methacrylate/methacrylic acid, VP/hexadecene, VP/triacontene, VP/styrene or VP/acrylic acid/lauryl methacrylate copolymers or butylated polyvinylpyrrolidone (PVP),
copolymers of a vinyl ester and preferably vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate or allyl dimethylpropionate/vinyl stearate copolymers,
hydrogenated or nonhydrogenated polyolefins and preferably polymers or copolymers of $C_2$-$C_{20}$ alkenes, such as polybutenes, polyisobutenes or polydecenes,
alkylcelluloses and preferably alkylcelluloses carrying a $C_2$-$C_6$ alkyl group, such as ethylcellulose and propylcellulose,
polyvinyl alcohols, and
their mixture(s).

According to a specific embodiment, the nonsilicone film-forming polymer represents from 0.5% to 10% and more particularly still from 1% to 5%, by weight, of the total weight of the composition.

According to another specific embodiment, the composition according to the invention can also comprise a coloring material chosen in particular from pigments and pearlescent agents.

The pigments can be in the pulverulent or powder form and, according to one alternative form, they exhibit a mean diameter not exceeding 200 µm and, according to another alternative form, not exceeding 150 µm.

The term "pigments" should be understood as meaning white or colored, inorganic or organic and coated or uncoated particles which are insoluble in an aqueous phase and which are intended to color and/or opacify the composition containing them. Mention may be made, among the pigments which can be used in the composition of the invention, of titanium dioxide, optionally surface treated, zirconium, zinc or cerium oxides, and also iron or chromium oxides, manganese violet, ultramarine blue, chromium hydrate, ferric blue, carbon black and their mixtures. It can also concern a pigment having a structure which can, for example, be of sericite/brown iron oxide/titanium dioxide/silica type. It can also concern pigments having a structure which can, for example, be of the type of silica microspheres containing iron oxide. Advantageously, the pigments of the invention are iron oxides and/or titanium dioxides.

The pigment particles can be surface treated by the deposition of an agent at the surface of the coloring material by evaporation of solvent, chemical reaction, or creation of covalent bonds between the surface agent and the treated particle. According to a specific alternative embodiment, the agent is a silicone or an amino acid. The pigment can be coated with a silicone layer, in particular with a methicone, dimethicone (also known as polydimethylsiloxane (PDMS)), hydrogenated dimethicone, dimethicone/methicone copolymer or acrylate/dimethicone copolymer layer and more particularly still with a dimethicone layer. According to another specific alternative embodiment, the pigment is chosen from iron oxides and/or titanium dioxides coated in a dimethicone layer.

According to a specific embodiment of the invention, the pigments or pearlescent agents, represent from 5% to 20% by weight and, according to an alternative form, from 5% to 15% by weight, with respect to the total weight of the composition.

The composition of the invention can also comprise at least one gelling compound different from the abovementioned silicone or nonsilicone polymers. This gelling agent, which makes it possible to structure the fatty phase based on volatile oil, is chosen in particular from natural or synthetic clays; modified natural micas, such as aluminum, magnesium and potassium fluorosilicate; esters of dextrin and of fatty acid, such as dextrin palmitate or dextrin myristate; mono- or polyglyceryl $C_8$-$C_{30}$ fatty acid triesters, such as glyceryl tri(hydroxystearate) (INCI name: Trihydroxystearin).

According to an alternative embodiment, the gelling compound of the invention is chosen from a natural or synthetic clay chosen from bentonites, in particular hectorites and montmorillonites, beidellites, saponites, nontronites, sepiolites, biotites, attapulgites, vermiculites and zeolites. In particular, the clay is chosen from hectorites. According to a specific alternative embodiment, use is made of hectorites modified with a quaternary alkylammonium chloride, said ammonium being substituted by at least one and in particular at least two $C_{14}$-$C_{20}$ alkyl radicals, such as disteardimonium hectorite, in which the ammonium comprises two methyls and two stearyls.

The gelling compound can represent from 0.05% to 10% and according to an alternative form from 0.1% to 5%, by weight, of the total weight of the composition.

According to another embodiment, the composition of the invention can also comprise any additive normally used in cosmetics, such as antioxidants, preservatives, fragrances, cosmetic active agents, such as, for example, emollients, moisturizing agents, vitamins, sunscreens, and their mixtures.

According to other embodiments, the composition of the invention can be in any cosmetic form conventionally used for applications to keratinous fibers or the skin, such as solid, liquid or even pressurized liquid forms. It can in particular be formulated in the form of a cream, of a gel or of an anhydrous product.

The composition of the invention can be prepared according to processes conventional for compositions comprising a volatile oil. The composition according to the invention is more particularly a mascara intended for making up keratinous fibers, in particular the eyelashes and the eyebrows. When the composition of the invention is intended for the formulation of mascaras, the process for the preparation of said composition can optionally comprise a milling stage in order to obtain a powder formed of fine solid particles. This milling stage can be carried out in a three roll mill, such as an Exakt 50i mill from Exakt Technologies.

According to another specific embodiment, the composition according to the invention is formulated in the form of an anhydrous mascara comprising the abovementioned compounds (i), (ii), (iii) and (iv).

The invention is also targeted at a method for making up and/or caring for keratinous substances comprising a stage of application to the keratinous substances, in particular the eyelashes, eyebrows, skin or lips, of a composition according to the invention.

Another subject matter of the invention is aimed at a film consisting of a composition according to the invention having in particular a thickness ranging from 150 to 800 μm.

Once dry, the film formed on the support is essentially devoid of volatile oil (iv).

An additional subject matter of the invention relates to the use of a composition according to the invention for making up and/or caring for keratinous substances, the skin or the lips, and more particularly in semipermanent mascaras, foundations and lipsticks.

Thus, the present invention also covers semipermanent mascaras and long-lasting foundations comprising a composition according to the invention. These makeup products combine hold, comfort and flexibility, for at least 24 hours. In particular, a mascara exhibits a hold of at least 24 hours, indeed even up to 36 h, and withstands a day, a night and a shower.

A final subject matter of the invention relates to a makeup kit comprising a composition according to the invention, packaged in a reservoir, and also to means for withdrawal and application of said composition to keratinous fibers, the skin and/or the lips.

The reservoir can be a bottle, a dish or a jar.

The withdrawal and application means can comprise a brush, including a fine brush, a sponge or a cellular foam.

Besides the preceding embodiments or alternative embodiments, the invention also comprises other embodiments or alternative embodiments which will emerge from the remainder of the description which follows, which relates to the preparation of compositions according to the invention which are given by way of illustration and which cannot in any way limit the scope of the invention. However, these examples are an integral part of the invention.

In the description and the claims, the percentages are given by weight, the temperature is expressed in degrees Celsius or is the ambient temperature of between 20 and 25° C., and the pressure is atmospheric pressure, unless otherwise mentioned.

EXEMPLARY EMBODIMENTS OF THE INVENTION

Example 1: According to the Invention

An anhydrous mascara is prepared according to the formula below (% by weight of the final composition).

| | |
|---|---|
| Trimethylsiloxysilylcarbamoyl pullulan | 3 |
| Silicone polymer | 5.4 |
| Polymethyl methacrylate or PMMA | 5 |
| Caprylyl methicone | 2 |
| Iron oxides | 5 |
| Isododecane | q.s. 100 |

The starting materials used are as follows:
Trimethylsiloxysilylcarbamoyl pullulan: TSPL-30-ID F® from Shin-Etsu Silicone,
polymethyl methacrylate: Sun PMMA X®
Silicone polymer: Gransil® PC-12/CD in the form of a predispersion of polysilicone-11 in isododecane having a solids content of 4.5%
Isododecane from Ineos Oligomers.
Procedure:
The silicone polymer is dispersed in the isododecane with the trimethylsiloxysilylcarbamoyl pullulan using an Ultra-Turrax stirrer at ambient temperature. The pigments milled beforehand using a three roll mill are added to the mixture and then, finally, the PMMA.

The composition obtained is a mascara. This mascara is applied to the eyelashes using an applicator. The evaporation of the isododecane makes possible the formation of a film on the keratin fibers. The film exhibits a flexible texture producing a feeling of comfort. The makeup rendering is a matte effect. The mascara can be retained for more than 24 h, and can withstand a period under the shower.

Example 2: According to the Invention

Example 1 is repeated, the PMMA being replaced with mica in the same proportions as mattifying filler.

An anhydrous mascara is prepared according to the formula below (% by weight of the final composition).

| | |
|---|---|
| Trimethylsiloxysilylcarbamoyl pullulan | 3 |
| Silicone polymer | 5.4 |
| Mica | 5 |
| Caprylyl methicone | 2 |
| Iron oxides | 5 |
| Isododecane | q.s. 100 |

Submica® mica supplied by Sensient

The process for the manufacture of the composition is identical. The composition obtained according to this same process is applied to the eyebrows in order to produce a makeup effect. The film formed exhibits a matte rendering. The hold of the formula is greater than 24 h.

Example 3: Comparative or Control Mascara

A comparative or control mascara is prepared according to the following formula:

| | |
|---|---|
| Trimethylsiloxysilylcarbamoyl pullulan | 3 |
| Polymethyl methacrylate | 5 |
| Caprylyl methicone | 2 |
| Iron oxides | 5 |
| Isododecane | q.s. 100 |

In the formula of example 1, the silicone polymer is replaced with its weight of isododecane in the comparative or control mascara composition.

Example 4: Comparative Tests

Visual Appearance

The two compositions according to the invention (Ex. 1 and 2) are stable at T0; the pigments do not settle out.

On the other hand, the composition of the comparative example is completely unstable at T0 (complete sedimentation of the pigments) as a result of a very low viscosity compared with that of the two compositions of the invention.

Mattness

Method: Spreading over a contrast chart, thickness of the film 100 μm then drying overnight. Measurements with the Novo Gloss Trio glossmeter according to 3 angles (20°, 60° and 85°), i.e. 9 measurements per formula at different points of the film.

Results:

The values obtained are shown in the table below.

| | 20° | 60° | 85° |
|---|---|---|---|
| Example 1 (invention) | 0.56 | 0.48 | 0.27 |
| Example 2 (invention) | 0.47 | 0.41 | 1.56 |
| Example 3 (comparative) | 1.48 | 1.38 | 1.17 |

The comparative formula exhibits a slightly less matte effect than the two compositions of the invention.

Flexibility

Method:

Pouring of the formula into a Teflon sheet 13×8 cm in size in order to have a dry film of 80 mg/cm², drying overnight at ambient temperature and then drying for 4 h in an oven at 40° C.

The film recovered in the mold is wound around a cylinder with a different diameter: 05 mm, 10 mm, 20 mm, 30 mm, 40 mm and 50 mm, beginning with the largest diameter down to the smallest. The smallest cylinder on which the film breaks is recorded.

The smaller the diameter, the more flexible the film.

Results:

| Example 1 (invention) | Example 2 (invention) | Example 3 (comparative) |
|---|---|---|
| film cracked in the mold, flexibility OK down to the 05 mm cylinder | film homogeneous in the mold, flexibility OK down to the 05 mm cylinder | film homogeneous in the mold but brittle on retrieval flexibility OK down to the 30 mm cylinder |

The two compositions according to the invention are more flexible than the comparative composition. This particularly advantageous property provides comfort on application of the same film on the skin.

GENERAL CONCLUSIONS WITH REGARD TO THE TESTS

The two compositions of the invention exhibit a stability which is significantly superior to the comparative composition. The superior flexibility measured for the compositions of the invention makes it possible to obtain a feeling of flexibility and of comfort when a composition in accordance with the invention is applied to the eyelashes or the eyebrows.

Furthermore, the mascaras formed by the compositions according to the invention have a duration of use which can range up to 36 hours.

The invention claimed is:

1. An anhydrous cosmetic composition, comprising:
   (i) from 0.5 to 30 weight percent of the total weight of the composition, of a trialkylsiloxysilylcarbamoyl pullulan compound;
   (ii) from 0.1 to 30 weight percent of the total weight of the composition of a silicone polymer obtained by reaction of an organopolysiloxane containing in particular at least one —Si—H group in the end position with an organopolysiloxane comprising at least one, better still at least two, ethylenically unsaturated groups bonded to a silicon atom, the ethylenically unsaturated group being chosen in particular from a vinyl, allyl or propenyl group which can be located at the ends of the organopolysiloxane molecule;
   (iii) from 0.5 to 30 weight percent of the total weight of the composition of a mattifying filler; and (iv) from 10 to 70 weight percent of the total weight of the composition of at least one volatile hydrocarbon oil.

2. The composition as claimed in claim 1, wherein the trialkylsiloxysilylcarbamoyl pullulan compound is a trialkylsiloxysilylcarbamoyl pullulan in which the alkyl groups are $C_1$-$C_6$ alkyl groups.

3. The composition as claimed in claim 1, wherein the trialkylsiloxysilylcarbamoyl pullulan compound is trimethylsiloxysilylcarbamoyl pullulan.

4. The composition as claimed in claim 1, wherein the silicone polymer (ii) is a non-gelled or gelled crosslinked silicone polymer in the form of gelled or non-gelled particles, having a mean size ranging between 10 and 200 microns.

5. The composition as claimed in claim 1, wherein the silicone polymer (ii) comprises a silicone elastomer exhibiting viscoelastic properties chosen in particular from polydimethylsiloxane (PDMS) (or dimethicone), methylpolysiloxane (MQ), vinylmethylpolysiloxane (VMQ), phenylvinylmethylpolysiloxane (PVMQ), fluorovinylmethylpolysiloxane (FVMQ) and their mixtures, it being possible for the silicone elastomer to be provided in the form of a gel, of a paste or of a powder.

6. The composition as claimed in claim 1, wherein the silicone polymer (ii) comprises polysilicone-11.

7. The composition as claimed in claim 1, wherein the mattifying filler (iii) is a solid filler in the pulverulent or powder form; the mattifying filler, having a volume-median diameter D50 of less than or equal to 25 μm.

8. The composition as claimed in claim 1, wherein the mattifying filler (iii) is a solid filler in the pulverulent or powder form; the mattifying filler, having a volume-median diameter D50 of less than or equal to 15 μm.

9. The composition as claimed in claim 1, wherein the mattifying filler (iii) consists of a solid filler in the pulverulent or powder form selected from the group consisting of:
cellulose powders, cellulose beads,
microcrystalline cellulose powders,
silica and silicate powders, amorphous silica microspheres, silica microbeads,
silica/$TiO_2$ composite powders,
talc/$TiO_2$/alumina/silica composite powders,
polymethyl methacrylate (PMMA) powders,
boron nitride powders,
crosslinked elastomeric organopolysiloxane powders coated or not coated with silicone resin,
hydrophobic silica aerogel powders,
nylon powders,
starch powders,
powders of vegetable origin, such as rice powders, cotton powders or silk powders,
talcs, natural and synthetic micas, sericites, borosilicates, and their mixtures.

10. The composition as claimed in claim 1, wherein the mattifying filler (iii) is selected from the group consisting of one or more polymethyl methacrylate (PMMA) powder(s), one or more mica(s) or their mixture(s).

11. The composition as claimed in claim 1, wherein the silicone polymer (ii) comprises polysilicone-11 gelled with isodecane.

12. The composition as claimed in claim 1, wherein the mattifying filler (iii) represents from 1% to 15% by weight of the total weight of said composition.

13. The composition as claimed in claim 1, wherein the mattifying filler (iii) represents from 1% to 10% by weight of the total weight of said composition.

14. The composition as claimed in claim 1, wherein said volatile hydrocarbon oil (iv) represents from 15% to 65% by weight of the total weight of the composition.

15. The composition as claimed in claim 1, wherein said volatile hydrocarbon oil (iv) represents from 20% to 60%, by weight of the total weight of said composition.

16. The composition as claimed in claim 1, wherein said volatile hydrocarbon oil (iv) represents the balance to 100% by weight of the total weight of the composition.

17. The composition as claimed in claim 1, wherein said volatile hydrocarbon oil (iv) comprises a mixture with a volatile silicone oil,
wherein the volatile hydrocarbon oil (iv) is selected from the group consisting of a branched alkane having from 8 to 16 carbon atoms, a branched ester having from 8 to 16 carbon atoms, and their mixture(s).

18. The composition as claimed in claim 1, wherein said volatile hydrocarbon oil (iv) is selected from the group consisting of an isoalkane having from 8 to 16 carbon atoms, comprising isododecane, isodecane or isohexadecane, of branched esters having from 8 to 16 carbon atoms, comprising isohexyl neopentanoate, and their mixture(s).

19. The composition as claimed in claim 17, wherein said volatile silicone oil is selected from the group consisting of a volatile linear silicone oil comprising hexamethyldisiloxane, octamethyltrisiloxane, decamethyltetrasiloxane, tetradecamethylhexasiloxane, hexadecamethylheptasiloxane and dodecamethylpentasiloxane; of a volatile cyclic silicone oil comprising cyclopentasiloxane, hexamethylcyclotrisiloxane, octamethylcylotetrasiloxane, decamethylcyclopentasiloxane and dodecamethylcyclohexasiloxane; and their mixture(s).

20. The composition as claimed in claim 1, wherein said volatile hydrocarbon oil (iv) is selected from the group consisting of isododecane, isohexadecane and their mixture(s) with a volatile silicone oil.

21. The composition as claimed in claim 17, wherein said volatile silicone oil
comprises cyclopentasiloxane.

22. The composition as claimed in claim 1, wherein said composition also comprises a non-silicone film-forming polymer selected from the group consisting of:
a copolymer of vinylpyrrolidone (VP) comprising at least one copolymer of VP and of a $C_2$-$C_{20}$ alkene;
a copolymer of a vinyl ester selected from the group consisting of vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, and their_mixture(s);
a hydrogenated or nonhydrogenated polyolefin, a poly(α-olefin) comprising a polymer or copolymer of a $C_2$-$C_{20}$ alkene;
an alkylcellulose carrying a $C_2$-$C_6$ alkyl group,
a polyvinyl alcohol, and
their mixture(s);
the non-silicone film-forming polymer represents from 0.5% to 10% by weight, with respect to the total weight of the composition.

23. The composition as claimed in claim 1, wherein said composition also comprises a nonsilicone film-forming polymer selected from the group consisting of:
- a copolymer of VP and of $C_2$-$C_{20}$ alkene, selected from the group consisting of VP/eicosene, VP/vinyl acetate, VP/ethyl methacrylate, VP/ethyl methacrylate/methacrylic acid, VP/hexadecene, VP/triacontene, VP/styrene or VP/acrylic acid/lauryl methacrylate copolymers and butylated polyvinylpyrrolidone, and their mixtures;
- a copolymer of a vinyl ester selected from the group consisting of vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, a allyl dimethylpropionate/vinyl stearate copolymer, and their mixtures;
- a polymer or copolymer of $C_2$-$C_{20}$ alkenes, selected from the group consisting of polybutene, polyisobutene, polydecene, and their mixtures;
- an alkylcellulose carrying a $C_2$-$C_6$ alkyl group, comprising ethylcellulose and propylcellulose,
- a polyvinyl alcohol, and
- their mixture(s);
- the nonsilicone film-forming polymer represents 1% to 5%, by weight, with respect to the weight of the composition.

24. The composition as claimed in claim 1, wherein said composition also comprises a coloring material selected from a pigment and a pearlescent agent representing from 5% to 20% by weight, with respect to the total weight of the composition.

25. The composition as claimed in claim 1, wherein said composition also comprises from 0% to 5%, by weight, of a wax selected from the group consisting of:
- a non-polar wax comprising a microcrystalline wax, a paraffin wax, ozokerite, a polyethylene wax, a silicone wax and a fluorinated wax;
- a polar wax, selected from the group consisting of beeswax, a rice bran wax, a carnauba wax, a candelilla wax, an ouricury wax, a Japan wax, a berry wax, a sumac wax, a montan wax, an esparto wax, a cork fiber wax, a sugarcane wax, an orange wax, a lemon wax, a laurel wax, a wax obtained by hydrogenation of an animal or vegetable oil having a linear or branched $C_8$-$C_{32}$ fatty chain, an olive oil esterified with stearyl alcohol, and a castor oil esterified with cetyl alcohol.

26. The composition as claimed in claim 25, wherein said wax obtained by hydrogenation of an animal or vegetable oil having a linear or branched C8-C32 fatty chain is selected from the group consisting of a jojoba oil, a sunflower oil, a castor oil, a coconut oil, a lanolin oil, an olive oil esterified with stearyl alcohol, and a castor oil esterified with cetyl alcohol; and
- their mixture(s).

27. The composition as claimed in claim 1, wherein said composition also comprises a gelling compound selected from the group consisting of a natural or synthetic clay; a modified natural mica; an ester of dextrin and of fatty acid; a mono- or polyglyceryl $C_8$-$C_{30}$ fatty acid trimester.

28. The composition as claimed in claim 1, wherein said composition also comprises a gelling compound selected from the group consisting of:
- a natural or synthetic clay selected from the group consisting of a bentonite, comprising a hectorite and montmorillonits, a beidellite, a saponite, a nontronite, a sepiolite, a biotite, an attapulgite, a vermiculite, a zeolite, a hectorite modified with a quaternary alkylammonium chloride, said ammonium being substituted by at least two $C_{14}$-$C_{20}$ alkyl radicals;
- a modified natural mica; an ester of dextrin and of a fatty acid; and
- a mono- or polyglyceryl $C_2$-$C_{30}$ fatty acid triester.

29. The composition as claimed in claim 1, wherein said composition also comprises a gelling compound selected from the group consisting of:
- a hectorite modified with a quaternary alkylammonium chloride, said ammonium being substituted by at least two $C_{14}$-$C_{20}$ alkyl radicals comprising a distearate hectorite in which the ammonium comprises two methyls and two stearyls;
- a modified natural mica selected from the group consisting of aluminum fluorosilicate, magnesium fluorosilicate, potassium fluorosilicate, and their mixture(s);
- an ester of dextrin and of a fatty acid selected from the group consisting of dextrin palmitate, dextrin myristate, and their mixture(s); and
- a mono- or polyglyceryl $C_8$-$C_{30}$ fatty acid trimester comprising glyceryl tri(hydroxystearate).

30. The composition as claimed in claim 27, wherein the gelling compound represents from 0.05% to 10% by weight, of the total weight of the composition.

31. The composition as claimed in claim 27, wherein the gelling compound represents from 0.1% to 5% by weight, of the total weight of the composition.

32. A product selected from the group consisting of a film, a mascara, a foundation and a lipstick, comprising a composition as claimed in claim 1, having a thickness of 150 to 800 μm.

33. A method for making up or a method for caring for keratinous substances, comprising applying to a keratinous substance selected from the group consisting of eyelashes, eyebrows, and skin, a composition as claimed in claim 1.

34. A makeup kit, comprising a composition as claimed in claim 1, packaged in a reservoir, and means for withdrawal and application of said composition to keratinous fibers, the skin and/or the lips.

35. An anhydrous cosmetic composition, comprising:
(i) from 0.5 to 30 weight percent of the total weight of the composition, of a triamethylsiloxysilylcarbamoyl pullulan compound;
(ii) from 0.1 to 30 weight percent of the total weight of the composition of a silicone polymer comprising polysilicone-11;
(iii) from 0.5 to 30 weight percent of the total weight of the composition of a mattifying filler selected from mica, a polymethylmethacrylate, or a mixture thereof; and
(iv) from 10 to 70 weight percent of the total weight of the composition of at least one volatile hydrocarbon oil comprising isododecane.

36. The cosmetic composition of claim 35, wherein the composition is formulated as a product selected from a film, a mascara, a foundation and a lipstick.

* * * * *